United States Patent [19]

Rabussay

[11] 4,355,022

[45] Oct. 19, 1982

[54] METHOD OF DENTAL TREATMENT

[75] Inventor: Dietmar P. Rabussay, Gaithersburg, Md.

[73] Assignee: Interon, Inc., Potomac, Md.

[21] Appl. No.: 279,536

[22] Filed: Jul. 1, 1981

[51] Int. Cl.³ .................... A61K 7/28; A61K 37/48
[52] U.S. Cl. .................................... 424/50; 424/54; 424/94; 132/89; 132/93
[58] Field of Search .................. 424/50, 54, 94, ; 128/89–93

[56] References Cited

U.S. PATENT DOCUMENTS

| Re. 30,675 | 7/1981 | Schole | 424/54 |
|---|---|---|---|
| 656,479 | 8/1900 | Schellenbach | 132/89 |
| 1,839,486 | 1/1932 | Lawton | 132/93 |
| 2,748,781 | 6/1956 | Collat | 132/93 |
| 2,975,102 | 3/1961 | Matsumura et al. | 424/54 |
| 3,004,897 | 10/1961 | Shore | 424/54 |
| 3,754,332 | 8/1973 | Warren | 132/93 |
| 3,771,536 | 11/1973 | Dragan | 132/89 |
| 3,830,246 | 8/1974 | Gillings | 132/89 |
| 3,855,142 | 12/1974 | Pader et al. | 252/135 |
| 3,929,579 | 12/1975 | Hoshimura et al. | 195/62 |
| 3,940,317 | 2/1976 | Katz et al. | 195/66 R |
| 3,985,869 | 10/1976 | Yoshimura et al. | 424/50 |
| 4,082,841 | 4/1978 | Pader | 424/50 |
| 4,104,125 | 8/1978 | Takechi et al. | 195/66 R |
| 4,140,758 | 2/1979 | Vidra et al. | 424/50 |
| 4,178,362 | 12/1979 | Hoogendoorn et al. | 424/48 |
| 4,231,381 | 11/1980 | Battista | 132/89 |
| 4,237,911 | 12/1980 | White | 132/89 |
| 4,283,385 | 8/1981 | Dhabhar et al. | 425/44 |

FOREIGN PATENT DOCUMENTS

| 490384 | 8/1938 | United Kingdom | 424/54 |
|---|---|---|---|
| 1033229 | 6/1966 | United Kingdom | 424/50 |

OTHER PUBLICATIONS

C.A. 93: 120254c, 112370x (1980) 91: 129026w (1979) 89: 123774a: 80122s (1978).
C.A. 89: 204016g (1978) 88: 41681h: 65993n: 58352z (1978) 87: 145649z (1977).
C.A. 87: 189474t: 189443g: 11641g (1977) 86: 12216p: 127293d (1977).
C.A. 83: 188245z (1975) 80: 124773a (1974) 79: 133838g (1973) 77: 156342p (1972).
C.A. 77: 838a (1972) 76: 49949z: 1651u (1972) 75: 52803g (1971) 74: 10681q (1971).
C.A. 74: 74874n: 130404y: 79691k (1971) 66: 27872k (1967) 59#387a (1963) 56#13030d (1962).

Primary Examiner—Shep K. Rose
Attorney, Agent, or Firm—Laurence R. Brown

[57] ABSTRACT

A dental and gum treatment agent and method uses the isolated and purified enzyme species lysozyme as a primary active substance to attack and destroy in situ the cariogenic bacteria in the oral cavity forming the plaque-calculus substrate and causing gum disorders. The agent operates to penetrate the bacterial cell wall and thereby destroy existing bacteria by disintegration so that residues are washed away. Auxiliary isolated enzymes of the groups of lipases, carbohydrases, phospholipases and proteases are used as additives to decrease treatment time as an aid to penetration of cell walls of gram (−) type bacteria. EDTA (ethylene diamino tetraacetic acid) is also used as an additive to remove ionic bonds that could clamp and stabilize bacterial walls to some extent after the lysozyme action. Thus, an aqueous solution of about 0.1 mg/ml of isolated lysozyme with or without controlled addition of known additives is effective in an oral cavity application for a few minutes to treat dental caries by removal of plaque and calculus, and to control gum infections.

6 Claims, No Drawings

METHOD OF DENTAL TREATMENT

TECHNICAL FIELD

This invention relates to the control of oral bacteria causing gum infections, plaque and calculus in dental treatment and more particularly it relates to the use of enzymes for degrading the peptidoglycan cell wall of bacteria in situ in the oral cavity so that bacteria are disintegrated and removed from the site.

BACKGROUND ART

It has been proposed that particular enzymes be used as an active agent for cleaning teeth. For example, U.S. Pat. Nos. to M. Pader 3,855,142, Dec. 17, 1974; 4,082,841, Apr. 4, 1978 has proposed that protease, carbohydrase, lipase or lipolytic enzymes may be used to reduce the rate of formation of dental plaque and calculus. Y. Yoshimura et al. U.S. Pat. Nos. 3,985,869, Oct. 12, 1976 and 3,929,579, Dec. 30, 1975, also propose that microorganisms belonging to the genus Streptomyces may be cultivated to derive enzymes used in undefined compositions for preventing and treating dental caries by lysing dental caries inducing cells such as streptococci and lactobacilli which are not lysed by egg-white lysozyme. H. Hoogendoorn et al. U.S. Pat. No. 4,178,362 - Dec. 11, 1979 propose that a glucose oxidase enzyme can form hydrogen peroxide to neutralize the pH values in the oral cavity and in tooth plaque. Also, oral compositions are proposed by J. Vidra et al. U.S. Pat. No. 4,140,758, Feb. 20, 1979 containing dextranase and a stabilizer/activator of manganese, calcium or magnesium ions. This is typical of the prior art development of enzymes for the treatment of dental caries and control of plaque and calculus.

However, these prior art treatment methods and agents are not satisfactory and have deficiencies. Thus, when the growth of the bacteria forming the plaque or calculus is arrested or slowed as by hydrogen peroxide treatment for example, the plaque substrate still exists. The actual killing and removal of plaque forming bacteria has been limited to particular species. Prior art enzyme treatment is primarily of that nature. However, it is more desirable to have a treatment which disintegrates and removes the plaque including the general types of cariogenic bacteria which cause its formation.

Many of the prior art treatments, such as the hydrogen peroxide generators, are to some extent toxic in the oral cavity and have harmful side effects to the mucous membrance or normal saliva constituency.

Other problems include the compositions and solutions necessary to carry the active ingredients of the prior art, which may be incompatible with the environment of the oral cavity, short lived or difficult to convey to all plaque locations, such as between teeth and the periodontal space. It is highly advantageous therefore rather to provide an active agent that is water soluble and compatible with the oral cavity saliva, etc. thereby to remain in situ for continued treatment and to reach all areas needing treatment.

A significant deficiency therefore of prior art treatment of dental caries is that the side effects enhance gum disorders rather than cure of gum disorders. It is known that some cariogenic bacteria types resident in the oral cavity are also the source of many of the gum diseases and disorders. However, the prior art attention to calculus and plaque seems to have developed cures inconsistent with simultaneous treatment of gum disorders.

Another deficiency is the length of time necessary for treatment, inconsistent with feasible application methods for prompt killing and removal of the bacteria.

A further significant problem is the presence in prior art enzyme treatments of undesired and unknown enzyme components e.g., proteases, which can make treatment ineffective and which make it very difficult to define proper dosages for prompt relief without serious side effects.

Thus, the present invention is directed to an improved method and agent for treatment for gum disorders, dental caries, plaque and calculus with specific active enzymes in a manner resolving deficiencies in the prior art enzyme treatment methods.

A specific object of the invention is to develop enzymes of a nature unharmful to mucous membranes of the oral cavity which will effectively and in a short application time kill and disintegrate those cariogenic bacteria generating gum disorders, dental caries and plaque.

Other features, objects and advantages of the present invention will be found throughout the following description and claims.

DISCLOSURE OF THE INVENTION

As is well known enzymes are very specific in their reactions and most of them act on just one kind of linkage. Thus, an enzyme may be used for confining a particular action to a particular compound or substance.

This invention provides such a specific enzyme as the primary agent for a treatment method for gum infections, dental caries and the destruction of plaque and calculus already formed as a substrate on the teeth or bone structure. It uses the lysozyme enzyme species as an active primary enzymatic polypeptide ingredient for the degradation, disintegration and removal of the cariogenic bacteria forming gum disorders, plaque and calculus substrate. Control of the plaque and calculus as is well known is essential to the treatment of dental caries, but the prior methods of retarding growth or neutralizing the substrate by active enzyme action without complete destruction and removal of the bacteria have not afforded the quick, thorough and effective treatment provided by this invention.

Thus, the enzyme literally attacks and penetrates the peptidogylcan bacterial cell walls common to the oral bacteria to be removed. This breaks down and destroys the bacteria by cleaving the peptidogylcan bonds by hydrolysis. Thus, the bacteria are killed and disintegrated (lysed) in such a way as to permit remaining fragments to be removed.

Reinforcement of the enzymatic action is afforded by specific associated enzymes and drugs as activating substances to produce quick effective treatment over the accelerated treatment period of a few minutes. Thus, the primary lysozyme enzyme alone destroys gram (+) type bacteria effectively. Auxiliary associated enzymes of the lipases, carbohydrases, phospholipases and protease species will concurrently degrade the gram (−) bacteria outer membrane (LPA layer) and make the cell wall accessible to the action of, and destruction by, lysozyme.

Also, the drug EDTA (ethylene diamino tetraacetic acid) aids in removing the binding action of $Ca^{++}$ and $Mg^{++}$ ions in the cell wall to remove any tendency of the wall to exist even with the primary wall bonds destroyed by the lysozyme.

Thus, the use of lysozyme as a primary active enzyme for mouth care treatment in control of gum disorders, dental caries, plaque and calculus is afforded by this invention. An improved fast acting enzyme is provided that can be applied without adverse reactions to the mucous surfaces to completely remove plaque and kill plaque forming bacteria when present in a plaque-calculus substrate and also be effective in control of oral bacteria causing gum disorders.

DETAILED DESCRIPTION OF PREFERRED EMBODIMENTS OF INVENTION

Decay of a tooth (dental caries) is caused by cariogenic bacteria which adhere to the tooth or bone structure in harbored areas and forms plaques or calculus. The plaques keep out substances harming the bacteria and permit sugar and fermentable carbohydrates to penetrate as an energy source for the growth of the cariogenic bacteria. These bacteria form acids dissolving tooth enamel, the first step to formation of cavities. Thus, control of the plaquescalculus and associated bacteria, hereinafter identified as cariogenic type bacteria, is essential to dental treatment. As aforesaid many of the same bacteria, which survive in the oral cavity, also cause gum disorders. As hereinbefore set forth the very restrictive action of enzymes has been proposed for control of plaque growth by such techniques as the generation of hydrogen peroxide as a counter agent.

However, in accordance with the present invention careful control of a specific enzyme is employed. Thus isolated pure lysozyme enzymes in appropriate concentrations attack the plaque problem in an effective manner without adverse side effects. They inactivate the cariogenic bacteria by destroying the bacterial cells by breaking down the cell wall structure (peptidoglycan) thereby disintegrating the bacteria into removable residue. Accordingly, the plaquecalculus structure is not merely controlled or retarded in growth, it is destroyed and removed and the bacteria causing gum disorders are no longer available.

Peptidoglycan has a bond between N-acetylglucosamine (G) and N-acetylmuramic acid (M). The Enzyme species lysozymes are those which actively react to cleave these particular G-M bonds. The peptidoglycan is the chemical compound which makes up the cell wall of all the oral cavity bacteria causing gum disorders and dental caries, which form two general classes, gram (+) with a thin outer layer of lipopolysaccharide (LPS) and gram (−) with a thick outer LPS layer. The lysozymes digest the gram (+) cell walls and leave small residue fragments, which results in damage and death to the cell which in that condition has no mechanical stability.

The thick LPS layer of gram (−) type bacteria present in some cases reduces the effectiveness of the lysozymes. Thus, other specific enzymes may be used as reinforcers for more rapid destruction of the gram (−) type bacteria. Enzymes of this type which are used to degrade the LPS layer are lipases and carbohydrases. Other enzymes which reinforce the action of lysozyme in degrading or damaging the cell membrane are phospholipases and proteases.

A drug which speeds up the lysozyme action and allows more complete collapse and destruction of the cell wall is EDTA (ethylene diamino tetraacetic acid). This drug has the characteristic of forming strong complexes with most divalent metal ions. In the peptidoglycan structure $Ca^{++}$ or $Mg^{++}$ can provide a binding force to provide some stability to the cell wall by acting as clamps which hold negatively charged residues of M and G together by ionic bonds. Thus, the cell wall disintegrates more rapidly and more thoroughly to lyse the cells with the clamps removed.

Thus, the lysozyme species of enzymes are used in accordance with this invention as the primary active component in mouth care treatment and products which both control microbial growth and destroy and remove bacteria from plaquecalculus substrates and in all associated gum areas of the oral cavity. The lysozymes can be used alone or with associated enzyme species and drugs as aforesaid to produce rapid acting destruction of the harmful cariogenic plaque forming bacteria.

The lysozymes are water soluble and are thus carried into otherwise inaccessible areas of the mouth in aqueous solutions thus treating small lesions and harbored surfaces which tend to accumulate plaque. Also the broken down bacterial residue is easily removed and is not simply surface sealed or temporarily neutralized as with other bacteriocidal substances formerly used.

Also the lysozymes are to some small concentration already present in the saliva and will not harm mucous surfaces. Lysozyme is not a foreign substance such as carried in previous products. The lysozymes thus support rather than destroy useful enzymes present in the mouth and saliva.

Lysozymes can be produced, for example, by the method set forth by K. Takechi et al. in U.S. Pat. No. 4,104,125, Aug. 1, 1978 or F. Katz et al. U.S. Pat. No. 3,940,317, Feb. 24, 1976.

It is pertinent in accordance with the disease control agent provided by this invention that complete control of the enzyme constituency be maintained by using well defined components to assure that only the desired enzyme constituents are present and that they are in the desired concentrations for fast effective lysing and removal of the cariogenic bacteria from the oral cavity.

EDTA is commonly known as a component of household cleaners, antiseptics, taste-stabilizers and food preservatives.

It is clear that this invention has therefore improved the state of the art with an improved gum disorder and dental caries treatment and product with faster action, little damage and more complete destruction of harmful mouth bacteria.

EXAMPLES

1. Lysozymes of controlled purity and concentration are isolated and then freeze-dried before being inserted in inert carrier substances in a concentration of about one-tenth milligram per milliliter of resulting solution in the mouth. this results in the disruption of most cariogenic bacterial cell walls in the oral cavity in a few minutes. The carrier substances preferably are wafers to be dissolved in water and used as a mouthwash, toothpaste, or toothpowder.

2. The same as 1, but with a lysozyme solution impregnated into dental floss or toothpicks used to carry the lysozymes in concentrated form into hard to reach oral crevices and gum areas to form in situ concentration of the enzymes for a reasonable resident time.

3. The same as 1, or 2 with addition of one or more species of carefully isolated enzymes of the group carbohydrases, lipases, phospholipases, and proteases in known concentrations. Similar dosage concentrations may be used in the oral cavity without damaging side effects.

4. The same as 1, 2 or 3 with the addition of EDTA in like concentration or less to act as an accelerator of lysozyme action and as a bacteriostatic substance.

5. The same as 4, with EDTA added in higher concentrations to act as a bacteriocidal substance.

6. The use of the substance prepared in 1 to 5 applied periodically when brushing teeth and retained in situ in the oral cavity on the plaque-calculus substrate for a period of several minutes before washing out with water to remove lysed bacterial residue.

INDUSTRIAL APPLICATION

A dental caries and gum disorder treatment agent and method may be used in water solution periodically on a daily basis to destroy and remove cariogenic bacteria from the oral cavity which cause gum disorders and plaque formations. The treatment agent prevents new plaque growth and has no harmful side effects. Application on dental floss of appropriate dosages permits treatment of gum disorders by gum contact in areas where the cariogenic bacteria are found, and leaves the treatment agent in residence for continued enzyme action. The lysozyme enzyme species which is already present in a small concentration in the oral cavity is isolated for purity, high concentration and in order to minimize side effects such as allergies and harm to the mucous membrane.

We claim:

1. The method of dental caries and gum treatment and for removing plaque and calculus comprising applying periodically in situ in the oral cavity on the plaquecalculus substrate or the gums an active material including an enzyme solution containing lysozyme of controlled purity and concentration of the class that materially degrades the peptidoglycan gram (+) cell walls of bacteria forming the substrate, so that bacteria are removed from the site including the step of using a lysozyme concentration in the solution of the order of one tenth milligram per milliliter, and applying the lysozyme in situ in the oral cavity in that concentration on the substrate thereby to remain resident on the substrate for a few minutes.

2. The method of claim 1 including the step of applying concurrently with the lysozyme further enzymes of the groups of lipases and carbohydrases which degrade the outer membrane of gram (−) bacteria, 3. The method of claim 1 wherein the step of applying enzymes comprises applying one or several enzymes that effectively disintegrate the outer membrane of gram (+) bacteria.

4. The method of claim 1 or 2 including the step of applying lysozymes with or without carbohydrases and lipases, in conjunction with one or more enzymes of the species phospholipases and/or proteases.

5. A dental treatment agent for use in the control of dental caries and gum disorders by selective destruction of cariogenic bacteria in the oral cavity comprising a mixture of isolated active enzymes of controlled purity of the lysozyme species in aqueous solution with a concentration of isolated lysozyme in the order of one tenth milligram per milliliter and one or several enzymes of the carbohydrase, phospholipase, lipase or protease species with materials forming a water soluble substance compatible with the saliva and oral cavity environment thereby for application to reach all dental surfaces and gums and to reside in situ in the oral cavity for continued action for a period of a few minutes after application.

6. The agent of claim 5 in aqueous solution with a concentration of isolated lysozyme in the order of one tenth milligram per milliliter.

* * * * *